United States Patent
Isoda et al.

(10) Patent No.: US 10,274,558 B2
(45) Date of Patent: Apr. 30, 2019

(54) MAGNETIC RESONANCE IMAGING APPARATUS

(71) Applicants: KYOTO UNIVERSITY, Kyoto-shi, Kyoto (JP); TOSHIBA MEDICAL SYSTEMS CORPORATION, Otawara-shi, Tochigi (JP)

(72) Inventors: Hiroyoshi Isoda, Kyoto (JP); Koji Fujimoto, Kyoto (JP); Hiroshi Kusahara, Tochigi (JP)

(73) Assignees: KYOTO UNIVERSITY, Kyoto-Shi, Kyoto (JP); TOSHIBA MEDICAL SYSTEMS CORPORATION, Otawara-Shi, Tochigi (JP)

( * ) Notice: Subject to any disclaimer, the term of this patent is extended or adjusted under 35 U.S.C. 154(b) by 800 days.

(21) Appl. No.: 14/878,126

(22) Filed: Oct. 8, 2015

(65) Prior Publication Data

US 2016/0033593 A1 Feb. 4, 2016

Related U.S. Application Data

(63) Continuation of application No. PCT/JP2014/059285, filed on Mar. 28, 2014.

(30) Foreign Application Priority Data

Apr. 8, 2013 (JP) ................................. 2013-080680

(51) Int. Cl.
*G01V 3/00* (2006.01)
*G01R 33/36* (2006.01)
(Continued)

(52) U.S. Cl.
CPC ............ *G01R 33/36* (2013.01); *A61B 5/0055* (2013.01); *A61B 5/055* (2013.01); *A61B 5/4244* (2013.01);
(Continued)

(58) Field of Classification Search
CPC ....................................................... G01R 33/36
(Continued)

(56) References Cited

U.S. PATENT DOCUMENTS

| | | |
|---|---|---|
| 5,332,968 A | 7/1994 | Brown |
| 5,410,250 A | 4/1995 | Brown |

(Continued)

FOREIGN PATENT DOCUMENTS

| | | |
|---|---|---|
| CN | 102018511 A | 4/2011 |
| JP | 7-505805 | 6/1995 |

(Continued)

OTHER PUBLICATIONS

International Search Report for PCT/JP2014/059285 dated Jun. 17, 2014, two pages.
(Continued)

*Primary Examiner* — Louis M Arana
(74) *Attorney, Agent, or Firm* — Nixon & Vanderhye P.C.

(57) ABSTRACT

A magnetic resonance imaging apparatus according to an embodiment includes sequence controlling circuitry and image generating circuitry. The sequence controlling circuitry acquires magnetic resonance signals in an imaging region. The image generating circuitry generates an image. The sequence controlling circuitry sets timings of RF pulses such that a first time and a second time are different. Here, the first time is a time since an irradiation of a first RF pulse without selection of region until a start of acquisition. The second time is a time since an irradiation of a second RF pulse with selection of the labeling region until the start of acquisition. The second time is also a time for a liquid present in the labeling region to reach a desired position in the imaging region. The first time is also a time for longitudinal magnetization components of a background tissue to become substantially zero.

9 Claims, 12 Drawing Sheets

(51) Int. Cl.
    *A61B 5/055*         (2006.01)
    *G01R 33/563*      (2006.01)
    *A61B 5/00*          (2006.01)
    *G01R 33/54*       (2006.01)
    *G01R 33/56*       (2006.01)
    *G01R 33/561*      (2006.01)
    *G01R 33/567*      (2006.01)

(52) U.S. Cl.
    CPC .......... *A61B 5/4325* (2013.01); *G01R 33/543* (2013.01); *G01R 33/56333* (2013.01); *G01R 33/5602* (2013.01); *G01R 33/5607* (2013.01); *G01R 33/5613* (2013.01); *G01R 33/5635* (2013.01); *G01R 33/5673* (2013.01)

(58) Field of Classification Search
    USPC ........................................ 324/306, 307, 309
    See application file for complete search history.

(56) References Cited

U.S. PATENT DOCUMENTS

| | | | |
|---|---|---|---|
| 8,583,212 | B2 | 11/2013 | Takei |
| 9,675,249 | B2* | 6/2017 | Miyazaki ........... G01R 33/5614 |
| 2008/0061780 | A1 | 3/2008 | Yamada et al. |
| 2009/0171186 | A1 | 7/2009 | Takei |
| 2010/0198053 | A1* | 8/2010 | Miyazaki ............... A61B 5/055 600/419 |
| 2011/0071382 | A1 | 3/2011 | Miyazaki et al. |
| 2011/0080170 | A1 | 4/2011 | Miyazaki |
| 2013/0293231 | A1 | 11/2013 | Hirai |
| 2013/0317348 | A1* | 11/2013 | Miyazaki ............... A61B 5/055 600/419 |
| 2016/0018501 | A1* | 1/2016 | Kimura ................ A61B 5/055 324/322 |

FOREIGN PATENT DOCUMENTS

| | | |
|---|---|---|
| JP | 2001-252263 | 9/2001 |
| JP | 2003-144416 | 5/2003 |
| JP | 2008-067857 | 3/2008 |
| JP | 2009-160122 | 7/2009 |
| JP | 2011-083592 | 4/2011 |
| JP | 2011-254905 | 12/2011 |
| WO | WO 2012/098955 | 7/2012 |

OTHER PUBLICATIONS

Non-English Written Opinion for PCT/JP2014/059285 dated Jun. 17, 2014, four pages.
Chinese office action dated Jun. 27, 2017, in Patent Application No. CN 201480012355.0.

* cited by examiner

MAGNETIC RESONANCE IMAGING APPARATUS

CROSS-REFERENCE TO RELATED APPLICATIONS

This application is a continuation of PCT international application Ser. No. PCT/JP2014/059285 filed on Mar. 28, 2014 which designates the United States, incorporated herein by reference, and which claims the benefit of priority from Japanese Patent Application No. 2013-080680, filed on Apr. 8, 2013, the entire contents of which are incorporated herein by reference.

FIELD

Embodiments described herein relate generally to a magnetic resonance imaging apparatus.

BACKGROUND

Magnetic resonance imaging is an imaging method in which the spins of atomic nuclei of a subject placed in a static magnetic field are magnetically excited with radio frequency (RF) pulses with the Larmor frequency, thereby generating an image from the data of magnetic resonance signals generated, accompanied by the excitation.

Magnetic resonance angiography (MRA) is drawing attention as one type of magnetic resonance imaging. In non-contrast MRA in which imaging is performed infusing a contrast agent, for example, the blood that has flown into a region of interest is selectively imaged by irradiating a labeling pulse to the blood in a labeling region that is set downstream in the blood vessels and, after a given time has passed, acquiring data on the region of interest. In the non-contrast MRA, however, it is difficult to acquire sufficient images in view of the contrast between the imaging of peripheral blood vessels and a background tissue.

DETAILED DESCRIPTION

A magnetic resonance imaging apparatus according to an embodiment includes sequence controlling circuitry and image generating circuitry. The sequence controlling circuitry acquires magnetic resonance signals in an imaging region after a given time has passed since an irradiation of a radio frequency (RF) pulse to a labeling region. The image generating circuitry generates an image using the magnetic resonance signals. The sequence controlling circuitry sets timings of RF pulses such that a first time and a second time are different. Here, the first time is a time since an irradiation of a first RF pulse without selection of region until a start of acquisition of the magnetic resonance signals. The second time is a time since an irradiation of a second RF pulse with selection of the labeling region until the start of acquisition of the magnetic resonance signals. The second time is also a time for a liquid present in the labeling region at a timing of the second RF pulse to reach a desired position in the imaging region. The first time is also a time for longitudinal magnetization components of a background tissue to become substantially zero. The background tissue is a tissue in the imaging region and is a tissue of other than a target of interest labeled by the irradiation of the second RF pulse.

With reference to the accompanying drawings, magnetic resonance imaging apparatuses (MRI apparatuses) according to embodiments will be described below. Embodiments are not limited to the embodiments to be described below. Furthermore, it is possible to apply the contents of the embodiments to be described below to other embodiments.

First Embodiment

Figure 1:
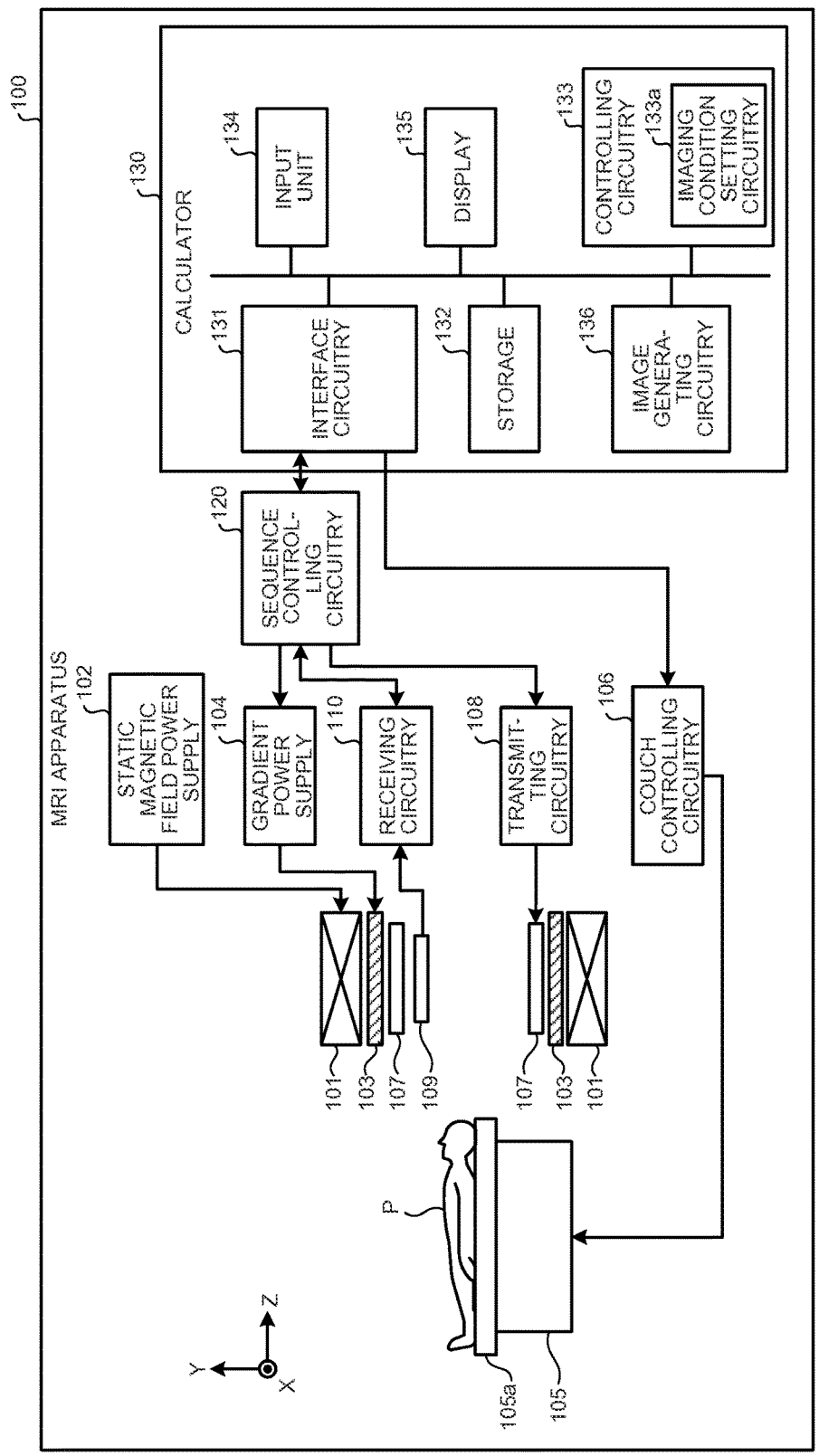
FIG. 1 is a block diagram representing a configuration of an MRI apparatus according to a first embodiment.

FIG. 1 is a block diagram representing a configuration of an MRI apparatus 100 according to a first embodiment. As shown in FIG. 1, the MRI apparatus 100 includes a static magnetic field magnet 101; a static magnetic field power supply 102; a gradient coil 103; a gradient power supply 104; a couch 105; couch controlling circuitry 106; a transmitting coil 107; transmitting circuitry 108; a receiving coil 109; receiving circuitry 110; sequence controlling circuitry 120; and a calculator 130. The MRI apparatus 100 does not include a subject P (such as a human body). The configuration shown in FIG. 1 is an exemplary only. For example, the units of the sequence controlling circuitry 120 and the calculator 130 may be configured integrally or separately.

The static magnetic magnet 101 is a hollow magnet that is formed in an approximately cylindrical shape and that generates a static magnetic field in the internal space. The static magnetic magnet 101 is, for example, a superconducting magnet that is magnetically excited with a current supply from the static magnetic field power supply 102. The static magnetic field power supply 102 supplies a current to the static magnetic magnet 101. The static magnetic magnet 101 may be a permanent magnet and, in this case, the MRI apparatus 100 does not necessarily include the static magnetic field power supply 102. The static magnetic field power supply 102 may be provided separately from the MRI apparatus 100.

The gradient coil 103 is a hollow coil that is formed in a cylindrical shape and that is disposed at the inner side with respect to the static magnetic magnet 101. The gradient coil 103 is formed by combining three coils that are orthogonal to one another and that correspond respectively to X, Y, and Z axes. Upon separately receiving current supplies from the gradient power supply 104, these three coils generate gradient fields whose magnetic intensities vary along the X, Y, and Z axes. The gradient fields of the respective X, Y, and Z axes generated by the gradient coil 103 are, for example, a slice encoding gradient field Gs, a phase encoding gradient field Ge, and a read-out gradient field Gr. The gradient power supply 104 supplies a current to the gradient coil 103.

The couch 105 includes a couchtop 105a on which the subject P is placed. Under the control of the couch controlling circuitry 106, the couchtop 105a is inserted into the hollow (imaging port) of the gradient coil 103 in a state where the subject P is placed on the couchtop 105a. In general, the couch 105 is set such that its longitudinal direction is parallel to the center axis of the static magnetic magnet 101. Under the control of the calculator 130, the couch controlling circuitry 106 drives the couch 105 to move the couchtop 105a in the longitudinal direction and the vertical direction.

The transmitting coil 107 is disposed at the inner side with respect to the gradient coil 103 and, upon receiving an RF pulse supply from the transmitting circuitry 108, generates a high-frequency magnetic field. The transmitting circuitry 108 supplies, to the transmitting coil 107, an RF pulse corresponding to a Lamor frequency that is determined according to the type of a targeted atom and the magnetic field intensity.

The receiving coil 109 is disposed at the inner side with respect to the gradient coil 103 and receives magnetic resonance signals (MR signals) that are emitted from the subject P due to the effect of the high-frequency magnetic field. Upon receiving an MR signal, the receiving coil 109 outputs the received MR signal to the receiving circuitry 110.

The transmitting coil 107 and the receiving coil 109 described above are an example only. They may be configured of one of, or a combination of, a coil having only a transmitting function, a coil having a receiving function, and a coil having transmitting and receiving functions.

The receiving circuitry 110 detects the MR signal that is output from the receiving coil 109 and generates MR data based on the detected MR signal. Specifically, the receiving circuitry 110 generates MR data by performing digital conversion on the MR signal output from the receiving coil 109. The receiving circuitry 110 transmits the generated MR data to the sequence controlling circuitry 120. The receiving circuitry 110 may be disposed at the side of the gantry including the static magnetic magnet 101 and the gradient coil 103.

The sequence controlling circuitry 120 images the subject P by driving the gradient power supply 104, the transmitting circuitry 108, and the receiving circuitry 110 according to the sequence information transmitted from the calculator 130. The sequence information is information that defines a procedure of performing imaging. The sequence information defines the intensity of a current to be supplied from the gradient power supply 104 to the gradient coil 103, the timing at which the current is supplied, the intensity of the RF pulse supplied from the transmitting circuitry 108 to the transmitting coil 107, the timing of the RF pulse, and the timing at which the receiving circuitry 110 detects the MR signal. For example, the sequence controlling circuitry 120 is an integrated circuit, such as an application specific integrated circuit (ASIC) or a field programmable gate array (FPGA), or an electronic circuit, such as a central processing unit (CPU) or a micro processing unit (MPU).

Upon receiving the MR data from the receiving circuitry 110 as a result of imaging the subject P by driving the gradient power supply 104, the transmitting circuitry 108, and the receiving circuitry 110, the sequence controlling circuitry 120 transfers the received MR data to the calculator 130.

The calculator 130 controls the whole MRI apparatus 100 and generates images and the like. The calculator 130 includes interface circuitry 131, storage 132, controlling circuitry 133, an input unit 134, a display 135, and an image generating circuitry 136.

The interface circuitry 131 transmits sequence information to the sequence controlling circuitry 120 and receives MR data from the sequence controlling circuitry 120. Upon receiving the MR data, the interface circuitry 131 stores the received MR data in the storage 132. The MR data stored in the storage 132 is arranged in a k-space by the controlling circuitry 133. As a result, the storage 132 stores k-space data.

The storage 132 stores the MR data received by the interface circuitry 131, the k-space data arranged in the k-space by the controlling circuitry 133, the image data generated by the image generating circuitry 136, etc. For example, the storage 132 is a semiconductor memory device, such as a random access memory (RAM) or a flash memory, a hard disk, or an optical disc.

The input unit 134 receives various instructions and information inputs from an operator. The input unit 134 is, for example, a pointing device, such as a mouse or a trackball, or an input device, such as a keyboard. Under the control of the controlling circuitry 133, the display 135 displays a graphical user interface (GUI) of receiving inputs of imaging conditions and an image generated by the image generating circuitry 136. The display 135 is, for example, a display device, such as a liquid crystal monitor.

The controlling circuitry 133 controls the whole MRI apparatus 100 and controls image capturing, image generation, image display, etc. As shown in FIG. 1, the controlling circuitry 133 includes an imaging condition setting circuitry 133a. The imaging condition setting circuitry 133a receives inputs of imaging conditions on the GUI and generates sequence information according to the received imaging conditions. The imaging condition setting circuitry 133a transmits the generated sequence information to the sequence controlling circuitry 120. For example, the controlling circuitry 133 is an integrated circuit, such as an ASIC or a FPGA, or an electronic circuit, such as a CPU or a MPU.

The image generating circuitry 136 reads the k-space data from the storage 132 and generates an image by performing reconstruction processing, such as the Fourier transform, on the read k-space data.

Figure 2:
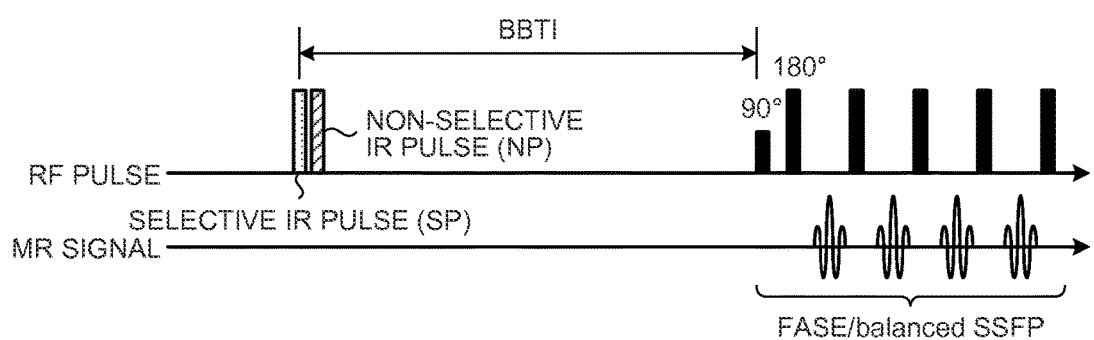
FIG. 2 is a pulse sequence diagram of explaining the Time-SLIP method.

FIG. 2 is a pulse sequence diagram of explaining the Time-SLIP (spatial labeling inversion pulse) method. FIG. 2 shows the relationship between timings of RF pulses and acquisition of MR signals. In the Time-SLIP method, in a labeling region set independently of an imaging region, an inversion recovery (IR) pulse inverting the longitudinal magnetization components of a tissue is irradiated to a fluid. Data in a region of interest is acquired at a time on which a given time has passed since the irradiation of the pulse, thereby a fluid flown into the region of interest being selectively imaged. In the Time-SLIP method, in addition to the IR pulse irradiated with selecting a labeling region, an IR pulse irradiated without selecting regions may be further used in combination. The former pulse is referred to as a selective IR pulse (SP) and the latter pulse is referred to as a non-selective IR pulse (NP). The selective IR pulse is also referred to as a labeling pulse or a tag pulse.

As shown in FIG. 2, in the normal Time-SLIP method, the sequence controlling circuitry 120 irradiates the non-selective IR pulse and the selective IR pulse almost simultaneously. Then, after a given time has passed since the irradiations of the pulses, the sequence controlling circuitry 120 acquires MR signals by using the fast asymmetric spin echo (FASE) method or the balanced steady-state free precession (SSFP) method. As shown in FIG. 2, the time from the irradiation of the IR pulse to the start of the acquisition of an MR signal is sometimes referred to as black-blood time to inversion (BBTI).

FIGS. 3A, 3B, 4A and 4B are pulse sequence diagrams explaining the relationship between a BBTI and an image in the Time-SLIP method. It is noted that, in FIGS. 3A and 4A, the longitudinal magnetization components of the blood to which the selective IR pulse has been irradiated in the labeling region and that has flown into the region of interest thereafter are represented by the solid line. On the other hand, the longitudinal magnetization components of a background tissue that is in the region of interest and that is other than a target of interest (e.g., the blood) are represented by the dotted line.

Figure 3A:
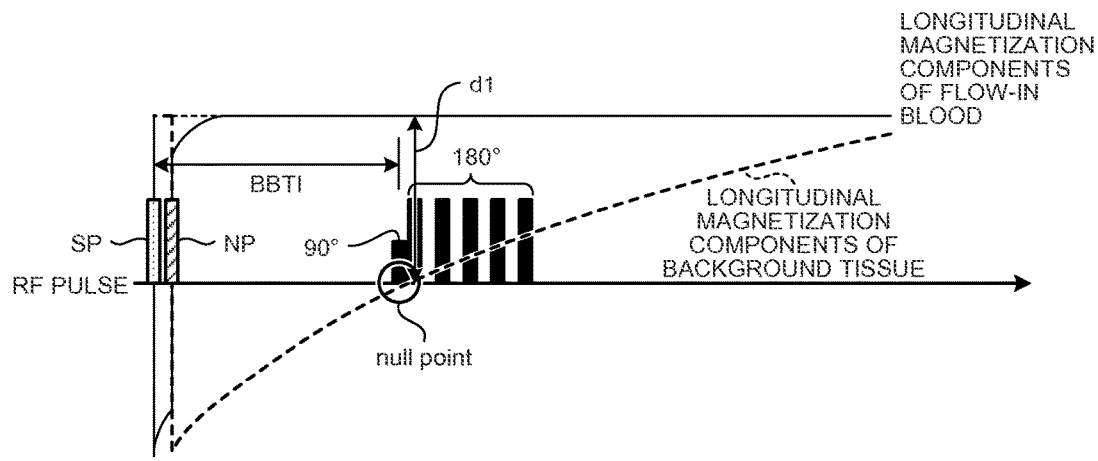
FIG. 3A and FIG. 3B are pulse sequence diagrams of explaining the relationship between a BBTI and an image.

In the first embodiment, it is assumed that the region of interest and the labeling region have, in principle, a positional relationship in which they are non-overlapping with each other, except for the case where they overlap a little due to their positional relationship. In this case, because the two IR pulses, i.e., the non-selective IR pulse and the selective IR pulse, are irradiated to the blood that has flown into the region of interest, the longitudinal magnetization components are inverted once and then inverted again as shown in FIG. 3A. On the other hand, because only one pulse, i.e., the non-selective IR pulse, is irradiated to the background tissue in the region of interest, the longitudinal magnetic components are inverted and then gradually recover as shown in FIG. 3A.

Figure 3B:
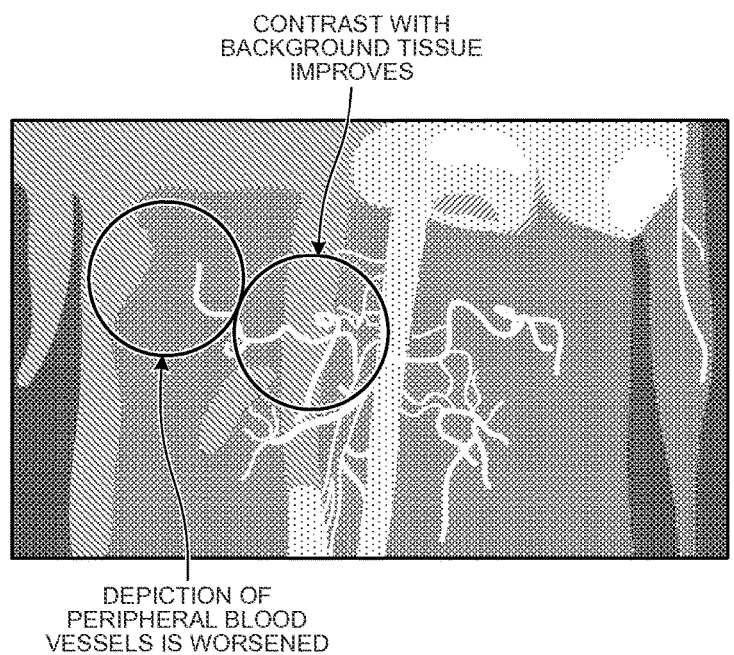

In the recovery process, there is a null point at which the longitudinal magnetization components of the background tissue are at "0". For example, as shown in FIG. 3A, when the BBTI is set in accordance with the null point, a difference d1 in the longitudinal magnetization components is caused between the blood having flown into the region of interest and the background tissue in the region of interest at the MR signal acquisition timing. In the image in that case, as shown in FIG. 3B, while the signals of the background tissue are reduced and the contrast between the blood vessels and the background tissue increases, the blood has not reached the periphery and the peripheral blood vessels are not imaged sufficiently. As a result, it is not possible to obtain a sufficient imaging power as a whole.

Figure 4A:
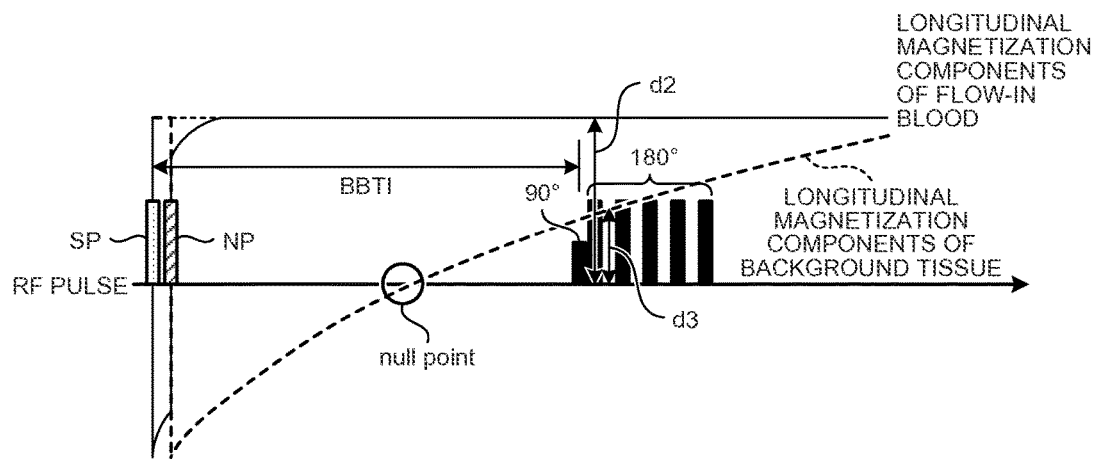
FIG. 4A and FIG. 4B are pulse sequence diagrams of explaining the relationship between a BBTI and an image.
Figure 4B:
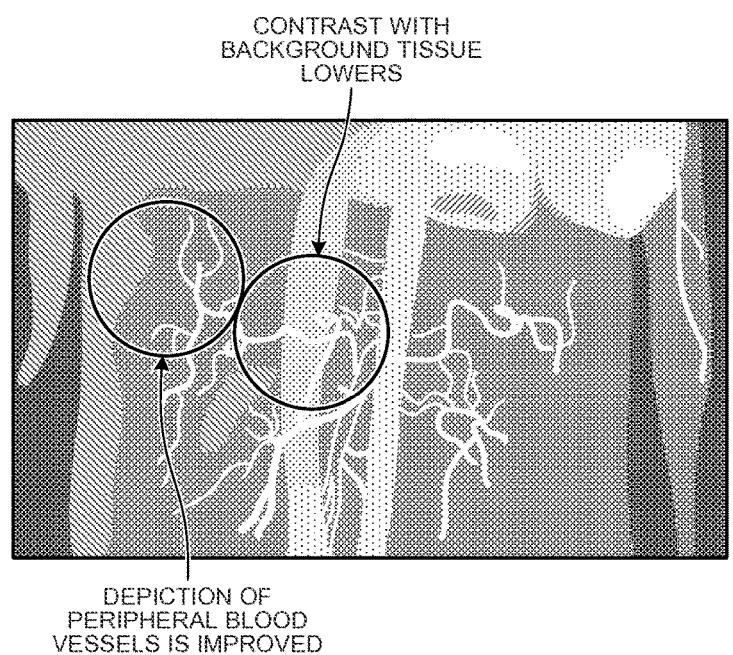

On the other hand, as shown in FIG. 4A, when the BBTI is extended later than the null point, there is only a difference between d2 and d3 as the difference in the longitudinal magnetization components between the blood having flown into the region of interest and the back ground tissue in the region of interest at the MR signal acquisition timing. In the image in this case, as shown in FIG. 4B, while the blood has reached the periphery and the peripheral blood vessels are imaged sufficiently, the signals of the background tissue recover and noise increases, the contrast between the blood vessels and the background tissue being worsened. As a result, it is not possible to obtain a sufficient imaging power as a whole.

According to the first embodiment, as described below, a method of independently setting a non-selective IR pulse irradiation timing and a selective IR pulse irradiation timing is proposed. In other words, the sequence controlling circuitry 120 sets the timings at which the two IR pulses are irradiated such that the wait time from the irradiation of the non-selective IR pulse until the start of the MR signal acquisition and the wait time from the irradiation of the selective IR pulse until the start of the MR signal acquisition are different from each other. The time from the non-selective IR pulse irradiation until the start of the MR signal acquisition is referred to as a first inversion time (TI) and the time from the selective IR pulse irradiation until the start of the MR signal acquisition is referred to as a second inversion time (TI).

Figure 5A:
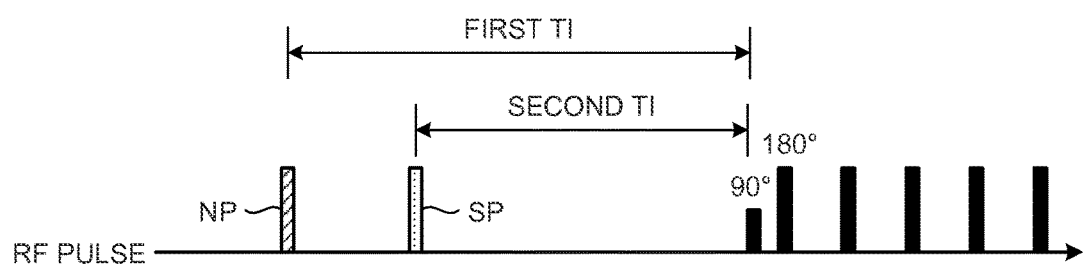
FIG. 5A and FIG. 5B are pulse sequence diagrams of explaining timings at which IR pulses are irradiated according to a first embodiment.
Figure 5B:
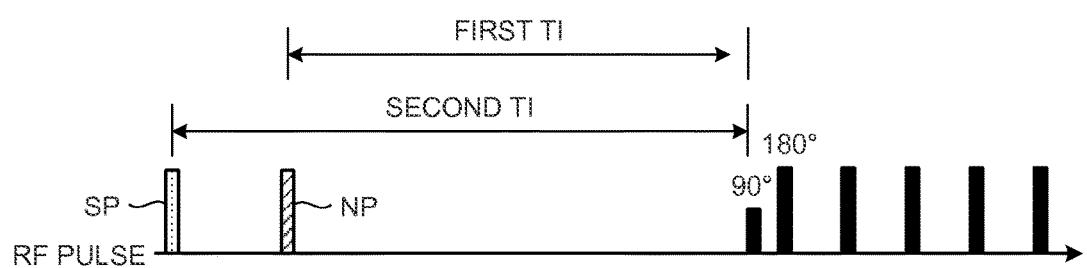

FIGS. 5A and 5B are pulse sequence diagrams of explaining the timings of the IR pulses according to the first embodiment. According to FIG. 5A, the non-selective IR pulse is first irradiated and then the selective IR pulse is irradiated. In this case, the first TI is longer than the second TI. According to FIG. 5B, the selective IR pulse is first irradiated and then the non-selective IR pulse is irradiated. In this case, the first TI is shorter than the second TI.

As described above, the sequence controlling circuitry 120 according to the first embodiment is capable of independently setting the timings of the two IR pulses regardless of the sequence in which the non-selective IR pulse and the selective IR pulse are irradiated. The sequence controlling circuitry 120 sets appropriate timings for two IR pulses, according to various conditions, such as, which site the region of interest is, at which position the labeling region is set, what the target of interest and the background tissue are, and how long the recovery time of the longitudinal magnetization components (the longitudinal relaxation time, the TI value) of the background tissue is, and the like.

For example, the sequence controlling circuitry 120 sets, for the first TI, a time until the longitudinal magnetization components of the background tissue becomes substantially zero (time until the null point). The sequence controlling circuitry 120 also sets, for the second TI, a time until the fluid present in the labeling region at the selective IR pulse irradiation timing reaches a desired position in the region of interest. In this case, the second TI is set independently of the first TI. Thus, it is possible that the second TI being set without being restricted by the longitudinal magnetization components of the background tissue. For example, it is possible to set, for the second TI, a time longer than the time estimated based on a recovery time of the longitudinal magnetization components of the background tissue (e.g., the time until the null point).

Exemplary imaging of acquiring an angiogram of arteries in the liver (the hepatic artery) by the MRI apparatus 100 according to the first embodiment will be described below.

Figure 6:
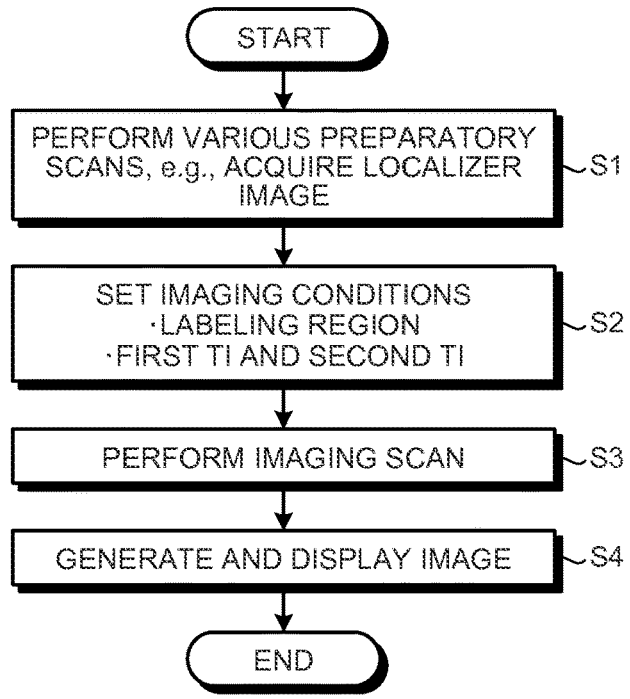
FIG. 6 is a flowchart of a procedure of processing according to the first embodiment.

FIG. 6 is a flowchart of a procedure of processing according to the first embodiment. In general, prior to the processing shown in FIG. 6, an operator selects a group of serial protocols of obtaining an angiogram of the hepatic artery (e.g., protocols of acquiring a localizer image, protocols of acquiring a sensitivity map, protocols of shimming, and protocols of an imaging scan). The sequence controlling circuitry 120 performs the various types of processing shown in FIG. 6 in accordance with the selected group of the series of protocols.

As shown in FIG. 6, the sequence controlling circuitry 120 performs various preparatory scans, e.g., acquires a localizer image, acquires a sensitivity map, and performs shimming (step S1).

The imaging condition setting circuitry 133a receives settings of imaging conditions, such as a labeling region, an imaging region, a first TI, and a second TI (step S2). For example, the imaging condition setting circuitry 133a displays the localizer image acquired at step S1 on the GUI and receives setting of a labeling region and an imaging region from the operator.

Figure 7:
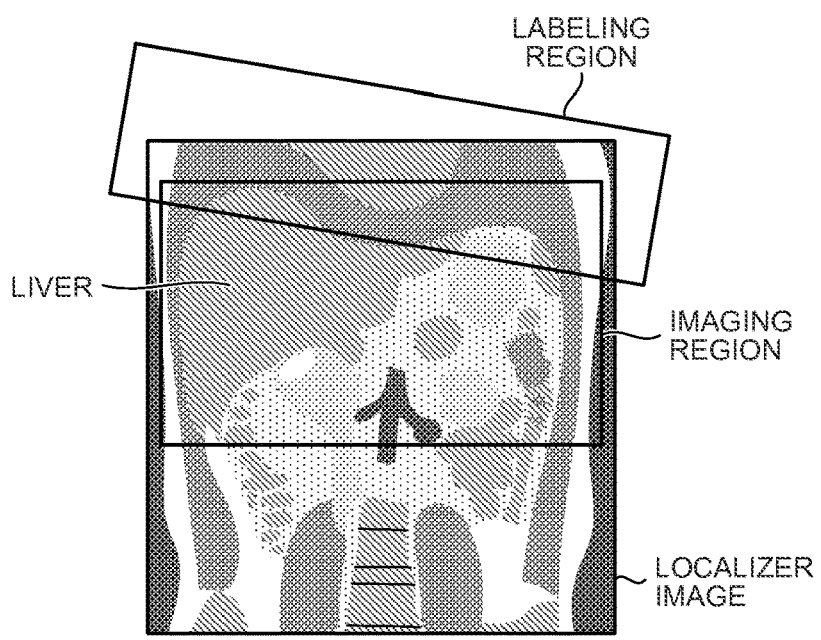
FIG. 7 is a diagram of explaining settings of a labeling region and an imaging region according to the first embodiment.

FIG. 7 is a diagram for explaining settings of a labeling region and an imaging region according to the first embodiment. In the first embodiment, the target of interest that is desired to be depicted in an image is the hepatic artery. For this reason, the operator sets, on the localizer image, an imaging region (a region from which MR signals to be imaged are acquired) such that the imaging region covers the liver. The operator sets a labeling region in a position such that, while the hepatic artery is selectively imaged, the effects of the hepatic vein and the portal vein are prevented as much as possible.

Figure 8:
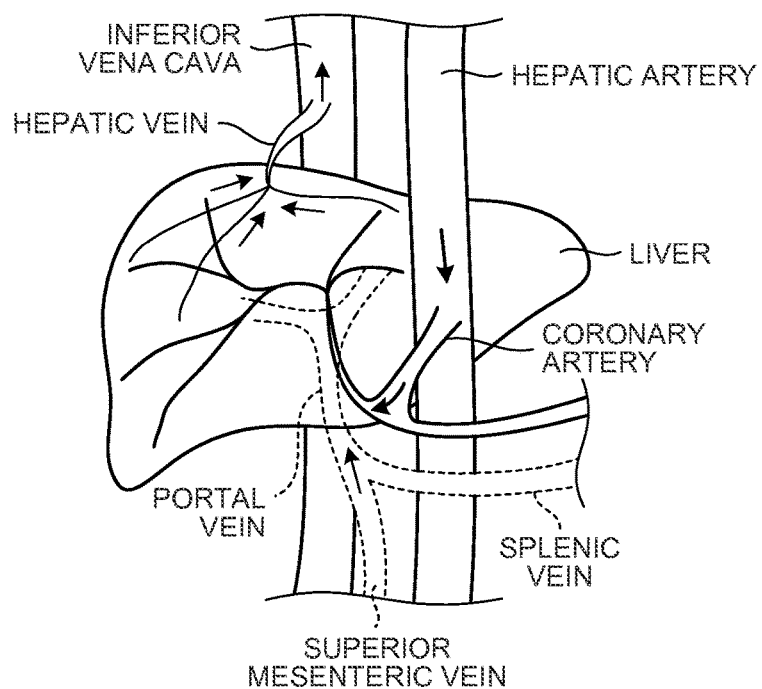
FIG. 8 is a diagram of explaining an anatomical structure of a liver.

FIG. 8 is a diagram of explaining an anatomical structure of the liver. As shown in FIG. 8, the blood flows into the liver from the hepatic artery and the portal vein and the blood flows out of the liver from the hepatic vein. In FIG. 8, the arrows denote the direction of the blood flow. In such a case, the labeling region is set, for example, as illustrated in FIG. 7, at a position along the top side of the liver. When the labeling region is set along the top side of the liver, the selective IR pulse is irradiated to the blood flowing through the aorta and the blood to which the selective IR pulse is irradiated flows downward into the liver as shown in FIG. 8. Meanwhile, the selective IR pulse is irradiated also to the blood flowing through the inferior vena cava and, because the blood to which the selective IR pulse is irradiated flows upward as shown in FIG. 8, there is no effect on the imaging of the hepatic artery.

The more the width of the labeling region (vertical width in FIG. 7) is increased, the more the amount of blood to which the selective IR pulse is irradiated in the aorta increases. In other words, because the amount of the flow of labeled blood increases, it is possible to increase the amount of the flow of blood that reaching the periphery within a given time. Needless to say, when the width is excessively increased and the labeling region overlaps the hepatic vein, the hepatic vein is also imaged, which is not preferable when the hepatic artery is selectively imaged.

In the first embodiment, the labeling region is set at a position along the top side of the liver and has some width. However, the width of the labeling region is limited to the extent that the labeling region is non-overlapping with the liver.

The imaging condition setting circuitry 133a independently receives the settings of the imaging conditions for the first TI and the second TI. For example, when an angiogram of the hepatic artery is acquired, the background tissue is the liver. According to the first embodiment, the first TI is, for example, 1200 msec based on the TI value of the liver. Furthermore, in order for the blood to reach the periphery, the second TI is, for example, 1600 msec. In this case, the second TI is longer than the time until the null point of the liver that is the background tissue. For example, the imaging condition setting circuitry 133a displays the GUI and receives inputs of the first TI of 1200 msec and the second TI of 1600 msec. Alternatively, when no input from the operator is received and the sequence controlling circuitry 120 executes the pulse sequence, the above-described values may be set automatically.

FIG. 6 will be referred back to here. When the setting of the imaging conditions ends, the sequence controlling circuitry 120 performs an imaging scan (step S3). According to the first embodiment, breath synchronized imaging of performing imaging in synchronization with the breathing by the subject P is employed. The liver that is the region of interest is relatively heavily affected by the motion of the body associated with the breathing. Furthermore, for example, when 3D volume data is acquired, MR signals are acquired over multiple breaths. For this reason, according to the first embodiment, in order to reduce the misregistration, the breath synchronized imaging is performed to acquire MR signals at the same breathing phase of the respiratory cycle.

Figure 9:
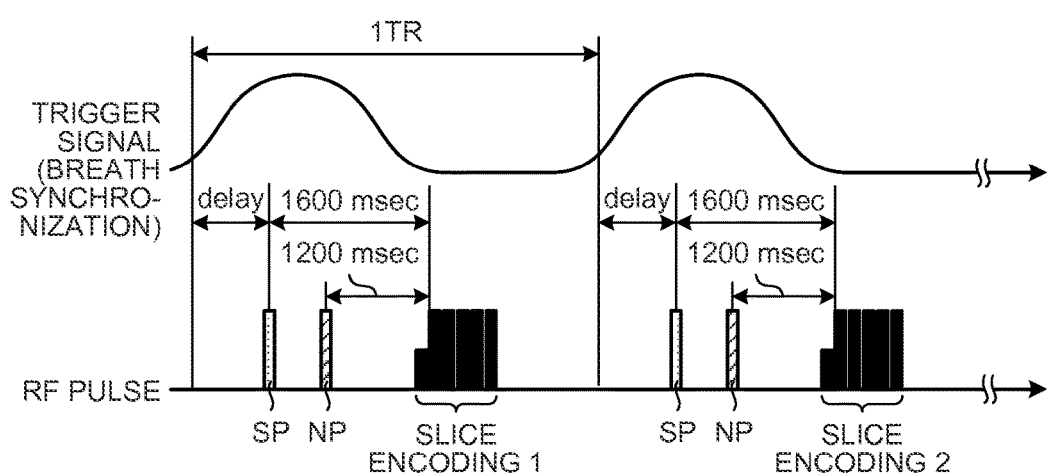
FIG. 9 is a pulse sequence diagram of explaining a pulse sequence according to a first embodiment.

FIG. 9 is a pulse sequence diagram for explaining a pulse sequence according to a first embodiment. In general, after a breathing practice is carried out, the subject P breaths according to an audio instruction (e.g., Inhale and Exhale). On the other hand, in response to the audio instruction serving as a trigger signal, or in response to the breathing motion detected by additionally monitoring the subject P serving as a trigger signal, the sequence controlling circuitry 120 performs the breath synchronized imaging as illustrated in FIG. 9.

For example, upon detecting a trigger signal at the beginning of inhaling, the sequence controlling circuitry 120 irradiates the selective IR pulse to the labeling region after a given delay time has passed since the trigger signal. After 400 mses (=1600 msec−1200 msec) has passed since the irradiation of the selective IR pulse, the sequence controlling circuitry 120 irradiates the non-selective IR pulse without selecting any region. After 1200 msec has passed since the irradiation of the non-selective IR pulse, the sequence controlling circuitry 120 acquires MR signals that correspond to, for example, one slice encoding from the imaging region by FASE, balanced SSFP, or the like. In FIG. 9, TR denotes the repetition time.

Although not illustrated in FIG. 9, the sequence controlling circuitry 120 may further irradiate a fat suppression pulse in order to suppress signals of the fat in the liver or subcutaneous fat. As methods of irradiating the fat suppression pulse, there are, for example, the chemical shift selective (CHESS) method, the short time inversion recovery (STIR) method, and the spectral presaturation with inversion recovery (SPIR) method.

The CHESS method is a method of acquiring MR signals after setting the center frequency of fat components for the center frequency of the pre-pulse to frequency-selectively suppress the fat components, using the difference of resonance frequencies of substances. The STIR method is a method of acquiring MR signals, by using the difference in the longitudinal relaxation time of substances, at a timing of inversion time at which the longitudinal magnetization components of the fat components become zero. The SPIR method is a method of suppressing the fat by inverting the longitudinal magnetization components of fat components by irradiating a frequency-selective pre-pulse.

When the fat suppression pulse is irradiated according to the CHESS method, it suffices if the sequence controlling circuitry 120 irradiates the fat suppression pulse just before starting acquisition of MR signals. When the fat suppression pulses according to the STIR method and the SPIR method are irradiated, the sequence controlling circuitry 120 further adjusts the TI and irradiates the fat suppression pulses. The sequence controlling circuitry 120 may non-selectively irradiate these fat suppression pulses without selecting any region, or may selectively irradiate the pulses with selecting a region inclusive of the imaging region.

Returning to FIG. 6, once the imaging scan is performed and the volume data of the liver is acquired, the image generating circuitry 136 generates an angiogram of the liver by using the acquired volume data and displays the angiography on the display 135 (step S4).

Figure 10:
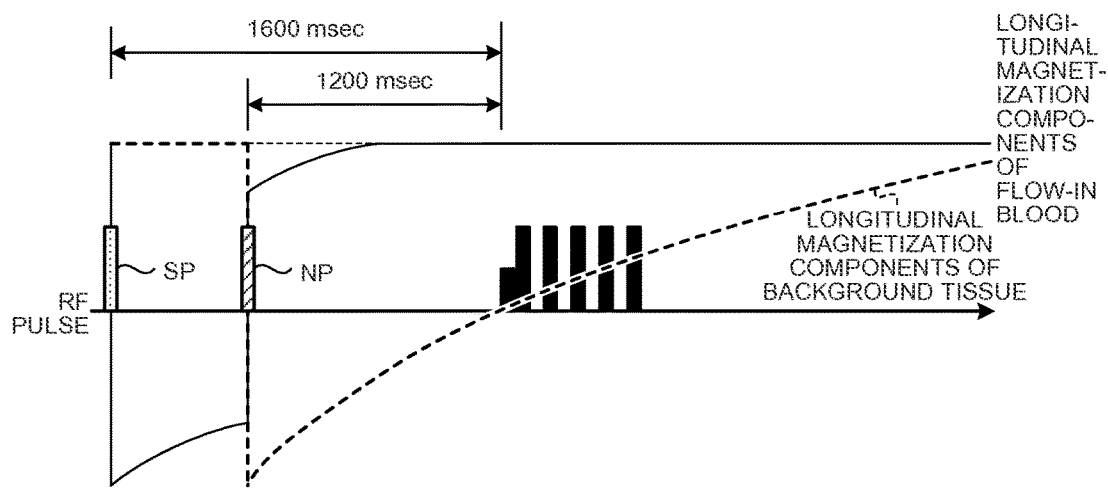
FIG. 10 is a pulse sequence diagram of explaining changes in the longitudinal magnetization components over time according to the first embodiment.
Figure 11:
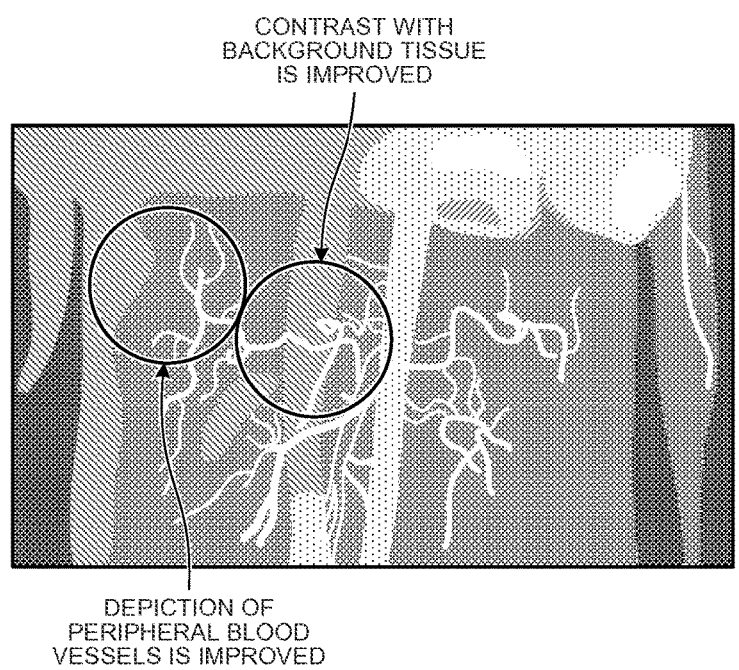
FIG. 11 is a diagram of explaining an angiogram of the liver according to the first embodiment.

FIG. 10 is a pulse sequence diagram of explaining changes in the longitudinal magnetization components over time according to the first embodiment. FIG. 11 is a diagram of explaining an angiogram of the liver according to the first embodiment. In FIG. 10, the longitudinal magnetization components of the blood to which the selective IR pulse is irradiated in the labeling region and that thereafter flows into the liver are denoted by the solid line. On the other hand, the longitudinal magnetization components of the liver that is the background tissue are denoted by the dotted line.

In the first embodiment, because the selective IR pulse is first irradiated to the labeling region, only the longitudinal magnetization components of the blood within the labeling region are inverted as shown in FIG. 10. The blood flows out of the labeling region while recovering its longitudinal magnetization components as shown in FIG. 10. Because the selective IR pulse is not irradiated to the liver that is the background tissue, the longitudinal magnetization components of the background tissue do not vary as shown in FIG. 10. After 400 msec, the non-selective IR pulse is then irradiated over the imaging region inclusive of the labeling region. Accordingly, as shown in FIG. 10, the longitudinal magnetization components of the background tissue are inverted, and the longitudinal magnetization components of the blood that have been once inverted and are in the recovery process are inverted again and each of them thereafter recovers.

The sequence controlling circuitry 120 acquires MR signals at the timing at which the longitudinal magnetization components of the background tissue are at the null point. Then, as shown in FIG. 10, because a sufficient difference in the longitudinal magnetization components occurs between the blood flowing into the region of interest and the background tissue in the region of interest, in the case of the image, the contrast between the blood vessels and the background tissue increases as shown in FIG. 11. The sequence controlling circuitry 120 irradiates the selective IR pulse at the timing for which the time for the blood to reach the periphery is taken into consideration. For this reason, in the image in this case, the peripheral blood vessels are sufficiently imaged as shown in FIG. 11.

As described above, according to the first embodiment, the sequence controlling circuitry 120 sets the IR pulse irradiation timing such that the first TI and the second TI differ from each other. In other words, in the first embodiment, by independently setting the non-selective IR pulse irradiation timing and the selective IR pulse irradiation timing, the time of suppressing the background tissue and the time of imaging the blood vessels (e.g., the periphery blood vessels) are controlled separately. As a result, according to the first embodiment, it is possible to perform imaging in the vicinity of the null point of the liver and to secure a sufficient blood flow-in time. In this manner, preferable images can be obtained in view of imaging of the peripheral blood vessels and the contrast with the background tissue, the imaging power in non-contrast imaging being improved.

Modification of First Embodiment

The first embodiment is not limited to the above-descried embodiment.

(Setting of Labeling Region)

For example, for the first embodiment, the case has been described where the labeling region is set at the position shown in FIG. 7 for the purpose of acquiring an angiogram of the hepatic artery; however, embodiments are not limited to this. The position at which the labeling region is set may be changed as appropriate in accordance with the target of interest, the anatomic individual difference, etc.

Figure 12:
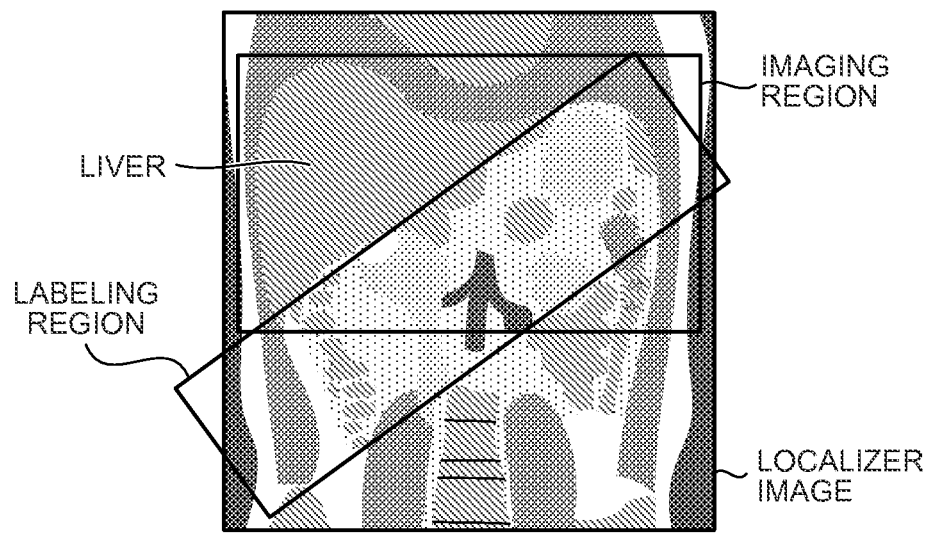
FIG. 12 is a diagram of explaining settings of a labeling region and an imaging region according to a modification of the first embodiment.

FIG. 12 is a diagram of explaining settings of a labeling region and an imaging region according to a modification of the first embodiment. In the modification, a target of interest that is desired to be imaged in an image is the portal vein. For this reason, an operator sets the labeling region at a position such that, while the portal vein is selectively imaged, effects from the hepatic artery and the hepatic vein are avoided as much as possible.

As shown in FIG. 8, the blood from the splenic vein and the superior mesenteric vein flows into the portal vein in the liver. In such a case, the labeling region is set, for example, at a position along the bottom side of the liver as shown in FIG. 12. When the labeling region is set at a position along the bottom side of the liver, the selective IR pulse is irradiated to the blood flowing through the splenic vein and the superior mesenteric vein and the blood to which the IR pulse is irradiated flows upward and flows into the liver as shown in FIG. 8. Meanwhile, the selective IR pulse is irradiated also to the blood flowing through the hepatic artery and, because the blood to which the selective IR pulse is irradiated flows rightward and does not flow into the liver as shown in FIG. 12, there is no effect on the imaging of the portal vein in the liver.

(Electrocardiogram Synchronization and Pulse Wave Synchronization)

For the first embodiment, the example where breath synchronized imaging is employed has been described; however, embodiments are not limited to this. The sequence controlling circuitry 120 may use, as a trigger signal, another biosignal, a clock signal of the MRI apparatus 100, or the like, instead of a breath. The sequence controlling circuitry 120 may combine the breath synchronization and the electrocardiogram synchronization (or the pulse wave synchronization). In this case, the sequence controlling circuitry 120 acquires MR signals at a timing at which both the breathing phase and the cardiac phase coincide. While improvement in the image quality is expected, extension of required imaging time is also expected.

(Processing Procedure)

For the first embodiment, the processing procedure has been described with reference to FIG. 6; however, embodiments are not limited to this. For example, the first TI and the second TI may be set, for example, at a stage prior to the processing shown in FIG. 6 (at a stage when an input that an angiogram of the hepatic artery is to be imaged is input).

Second Embodiment

A second embodiment will be described below. For the second embodiment, exemplary imaging of acquiring Han angiogram of the uterus will be described. The MRI apparatus 100 according to the second embodiment has a configuration similar to that of the MRI apparatus 100 according to the first embodiment and performs the processing procedure similar to that according to the first embodiment. The difference from the first embodiment will be mainly described below.

Figure 13:
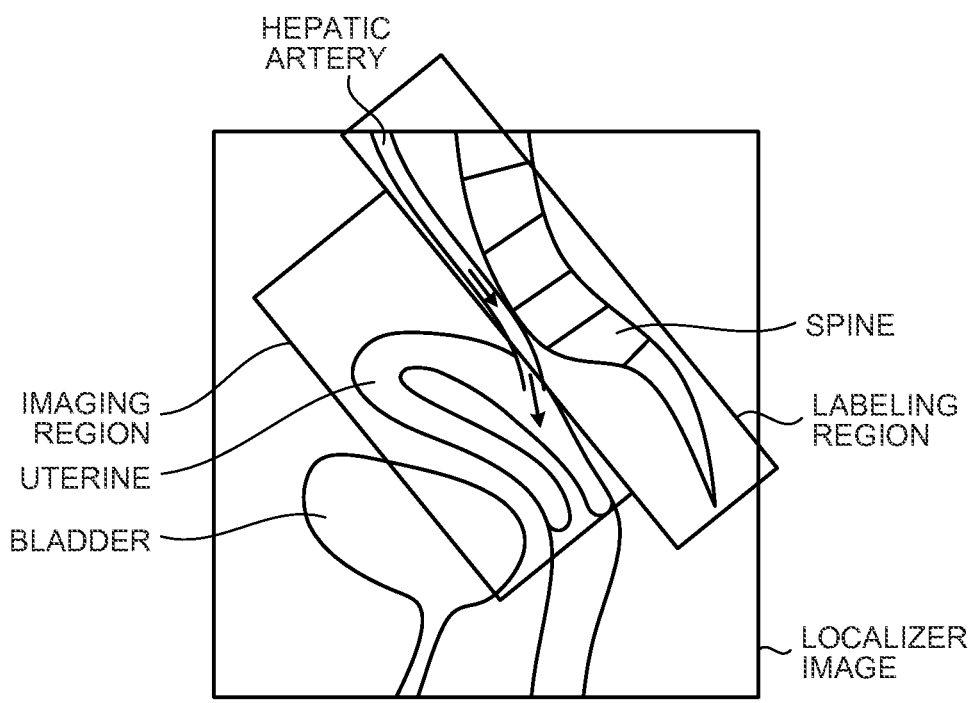
FIG. 13 is a diagram of explaining settings of a labeling region and an imaging region according to a second embodiment.

FIG. 13 is a diagram of explaining settings of a labeling region and an imaging region according to the second embodiment. According to the second embodiment, a target of interest that is desired to be imaged in an image is the blood in the uterus. For this reason, an operator sets an imaging region on a localizer image such that the localizer image is inclusive of the uterus that is a region of interest.

As shown in FIG. 13, the blood from the aorta flows into the uterus. The operator sets a labeling region at a position such that the labeling region is largely inclusive of the aorta while not overlapping the uterus. In general, as shown in FIG. 13, the labeling region and the imaging region are set at approximately parallel positions. The uterus may be oblique forward or backward due to the individual difference or being largely affected by the urine stored in the bladder. In such a case, it is also preferable that the labeling region be set such that the labeling region does not overlap the uterus.

Figure 14:
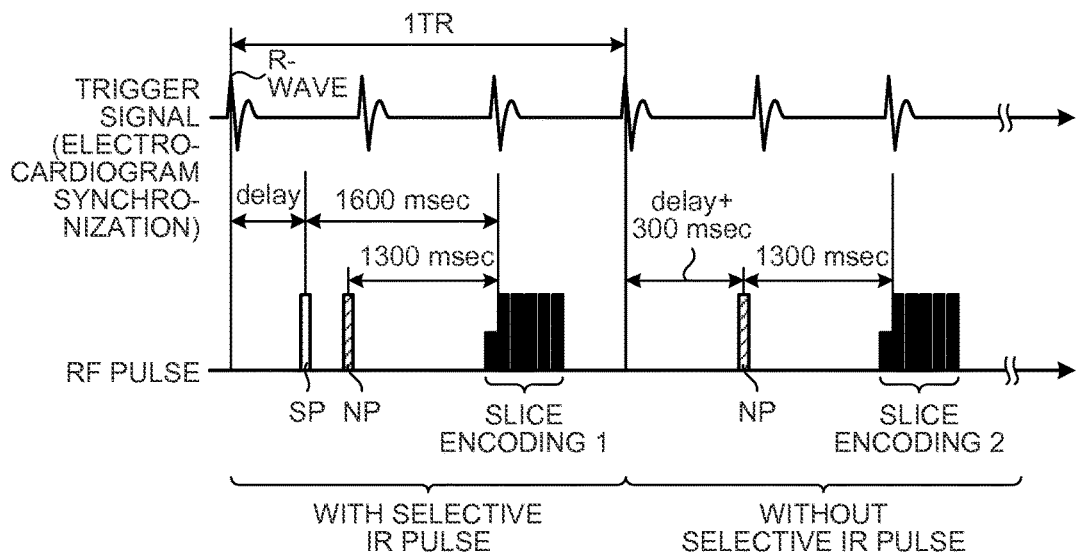
FIG. 14 is a pulse sequence diagram of explaining a pulse sequence according to the second embodiment.

FIG. 14 is a pulse sequence diagram of explaining a pulse sequence according to the second embodiment. As shown in FIG. 14, according to the second embodiment, instead of the breath synchronized imaging, electrocardiogram synchronized imaging of performing imaging in synchronization with the heart beats of the subject P is employed and a characteristic wave (such as an R-wave) is used as a trigger signal. According to the second embodiment, a subtraction method in which a difference between two images is calculated is employed in order to reduce the signals of the background tissue. These two points will be described in detail below. In the second embodiment, the first TI is set to be, for example, 1300 msec, based on a TI value of the uterus. Furthermore, the second TI is, for example, 1600 msec to increase the amount of blood flow into the uterus itself as much as possible.

In the second embodiment, one of the reason of employing the electrocardiogram synchronized imaging is that the uterus is not much affected by the body motion due to breathing compared to the liver.

The second reason is that, in the second embodiment, the electrocardiogram is used not only simply as a trigger signal but also employed aiming at increasing the amount of blood flow to be imaged. As in the case of the first embodiment, in the second embodiment, the non-selective IR pulse irradiation timing and the selective IR pulse irradiation timing are independently set. For example, as shown in FIG. 14, while the first TI is 1300 msec, the second TI is 1600 msec longer than the 1300 msec by 300 msec. In this manner, the second T1 time being extended by 300 msec, it is possible to increase the degree at which the blood reaches. Furthermore, if a larger number of the systole period of the heart pumping up large amount of blood is included, the effect that the amount of blood to be imaged is increased should be obtained.

As shown in FIG. 14, according to the second embodiment, there are two R waves and two systole periods since the irradiation of the selective IR pulse until acquisition of MR signals. Even when MR signals are acquired in the same second TI, as described above, by controlling a timing in combination with the electrocardiogram synchronization, it is possible to make an adjustment such that more R-waves are contained as many as possible. As a result, it is possible to increase the amount of blood flow imaged in an angiogram of the uterus and further improve the imaging power.

Next, the difference method will be described. The difference method is a method of acquiring an image obtained by subtracting the signals of the background tissue, in a way that, as for the same imaging slice, MR signals obtained by irradiating the selective IR pulse and MR signals obtained without irradiation of the selective IR pulse are acquired and calculates a difference between the two images generated respectively from the sets of the MR signals.

For example, as shown in FIG. 14, as for the same slice encoding, the sequence controlling circuitry 120 according to the second embodiment alternately repeats the TR in which the selective IR pulse is irradiated and the TR in which the selective IR pulse is not irradiated.

The TR in which the selective IR pulse is irradiated will be described. For example, in response to the R-wave serving as a trigger signal, the sequence controlling circuitry 120 irradiates the selective IR pulse to the labeling region after a given delay time has passed since the trigger signal. After 300 msec (=1600 msec−1300 msec) has passed since the irradiation of the selective IR pulse, the sequence controlling circuitry 120 irradiates the non-selective IR pulse without selecting any region. After 1300 msec has passed since the irradiation of the non-selective IR pulse, the sequence controlling circuitry 120 acquires MR signals corresponding to, for example, slice encode 1 by FASE, balanced SSFP, or the like. The successive time until the next trigger signal is referred to as 1TR.

The TR in which the selective IR pulse is not irradiated will be described. In response to the R-wave serving as the trigger signal, the sequence controlling circuitry 120 irradiates the non-selective IR pulse, without selecting a region, after the given delay time+300 msec has passed since the trigger signal. After 1300 msec has passed since the irradiation of the non-selective IR pulse, the sequence controlling circuitry 120 acquires MR signals corresponding to, for example, the same slice encoding 1 by FASE, balanced SSFP, or the like. The successive time until the next trigger signal is referred to as 1TR.

Although FIG. 14 does not illustrate, as for other slice encoding, the sequence controlling circuitry 120 alternately repeats the TR in which the selective IR pulse is irradiated and the TR in which the selective IR pulse is not irradiated. The difference method is not necessarily limited to the alternate repetition method. For example, after the whole volume data is acquired while the selective IR pulse is irradiated, the same whole volume data may be acquired without irradiation of the selective IR pulse.

Figure 15:
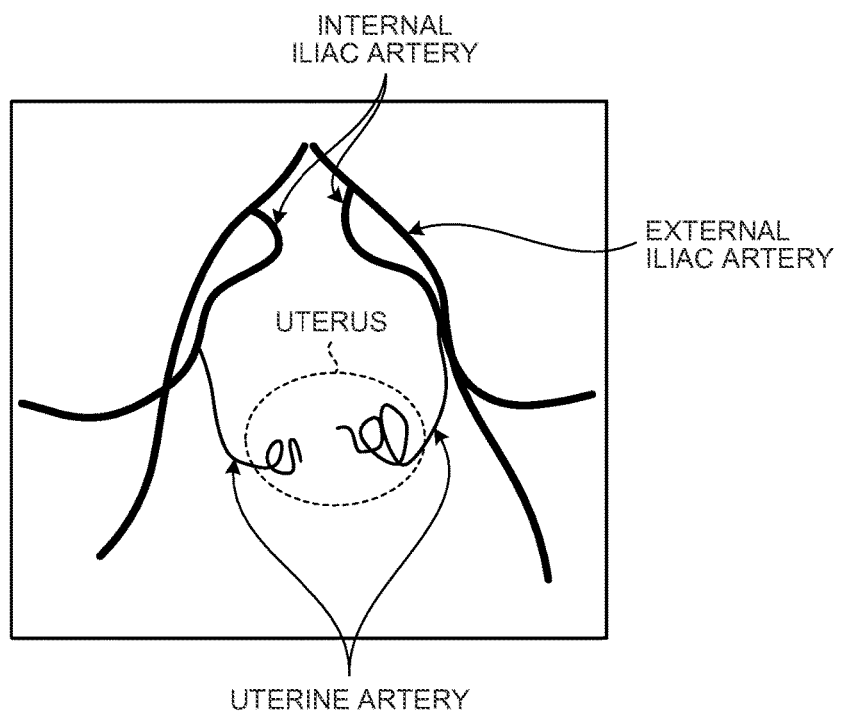
FIG. 15 is a diagram of explaining an angiogram (difference image) of the uterus according to the second embodiment.

FIG. 15 is a diagram of explaining an angiogram (difference image) of the uterus obtained by using the difference method in the second embodiment. In the difference method, by calculating a difference between an image acquired by irradiating the selective IR pulse (hereinafter, Han image with the selective IR pulse) and an image acquired without irradiation of the selective IR pulse (hereinafter, Han image without the selective IR pulse), the blood is imaged in black or imaged in white. Specifically, when the image with the selective IR pulse is subtracted from the image without the selective IR pulse, in the difference image, the blood vessels are imaged in black in the image. On the other hand, when the image without the selective IR pulse is subtracted from the image with the selective IR pulse, in the difference image, the blood vessels are imaged in white in the image. When the black and white of the difference image are inverted when the image is displayed, the black and white of the blood vessels in the image are also inverted. FIG. 15 exemplifies the angiogram of the uterus acquired by subtracting the image with the selective IR pulse from the image without the selective IR pulse, where the uterine artery is imaged in black.

According to the second embodiment, the first reason of employing the difference method is in the background tissue of the uterus. The background tissue of the uterus is, for example, the endometrium and the muscular layer around the uterus. Because the T1 values of them are slightly different from each other, even when the time until the null point of the background tissue is set for the first TI, there is a risk that the signals of the background tissue are not sufficiently suppressed and slightly remain. In this respect, according to the second embodiment, because the angiogram of the uterus is acquired by calculating the difference between the two images, it is assumed that it is possible to suppress, by the difference processing, the signals of the background tissue that have not been sufficiently suppressed and remain.

The second reason is in that, according to the second embodiment, because the signals of the background tissue are sufficiently suppressed in the image before the subtraction, the effects of the application of the difference method are more remarkable. When the difference method is employed, theoretically, it is assumed that the signals of the background tissue are subtracted to be substantially zero; however, practically, due to the effects of the motion and other various factors, when the signals of the background tissue remain in the image before the subtraction, even if the subtraction is performed, the signals do not necessarily become zero. The larger the signals of the background tissue remaining in the image before the subtraction are, the larger the effects of the motion and error are. In this respect, according to the second embodiment, because the time until the null point of the background tissue is set for the first TI, it is possible to constantly perform imaging in a state where the signals of the background tissue are close to zero and thus suppress the signals of the background tissue remaining in the image before the subtraction. As a result, when the subtraction is performed, error tends not to occur and it is possible to acquire a preferable image.

Modification of Second Embodiment

The second embodiment is not limited to the above-described embodiment. For example, according to the second embodiment, as in the case of the first embodiment, MR signals may be acquired and an image is generated by using a normal method not employing the difference method. The difference method may be applied to the first embodiment.

For the second embodiment, the example where the electrocardiogram synchronized imaging is employed has been described; however, embodiments are not limited to this. The sequence controlling circuitry 120 may use, instead of heartbeat, another biosignal, a clock signal of the MRI apparatus 100, or the like, as a trigger signal. Alternatively, the sequence controlling circuitry 120 may combine the electrocardiogram synchronization and the breath synchronization. Alternatively, pulse wave synchronization may be employed instead of electrocardiogram synchronization.

Third Embodiment

A third embodiment will be described. For the first and second embodiment, the case has been described where fixed values are used as the first TI and the second TI; however, embodiments are not limited to this. A method of setting a different first TI in accordance with the TR per individual and a method of calculating the first TI and the second TI in preparatory scans will be described. It is possible to combine the method to be described below with the above-described first and second embodiments or other embodiments as appropriate.

(Method of Setting Different First TI in Accordance with TR)

First of all, a method of setting a different first TI in accordance with the TR per individual will be described. For example, according to the first embodiment, application of the breath synchronized imaging of performing imaging in synchronization with the breathing of the subject P is assumed. In the breath synchronized imaging, in general, the respiratory cycle of the subject P is referred to as TR. Thus, the length of TR may differ depending on the individual; however, in this case, it is preferable to adjust the first TI due to the relationship with the recovery of the longitudinal magnetization components of the background tissue.

Figure 16A:
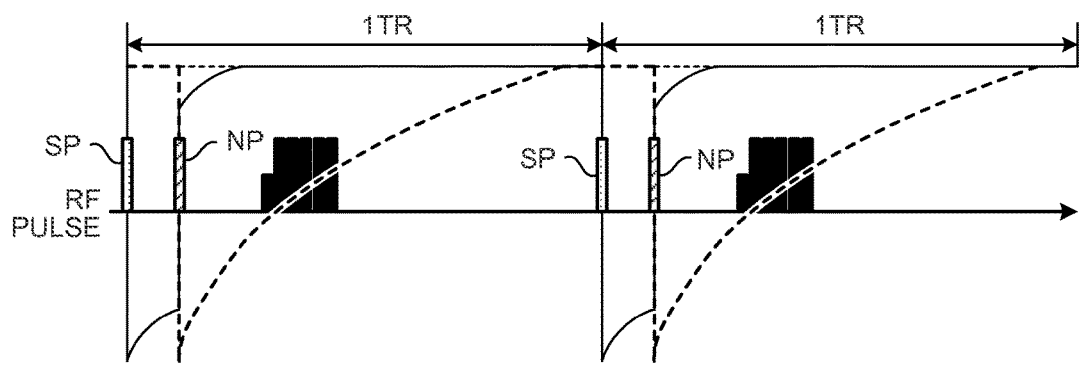
FIG. 16A is a pulse sequence diagram of explaining the relationship between a TR and a first TI according to a third embodiment.
Figure 16B:
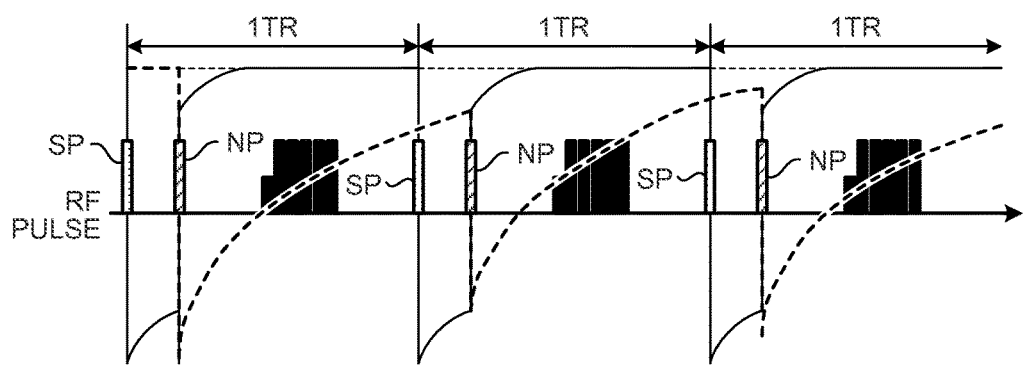
FIG. 16B is a pulse sequence diagram of explaining the relationship between a TR and a first TI according to the third embodiment.

FIG. 16A and FIG. 16B are pulse sequence diagrams of explaining the relationship between a TR and a first TI according to the third embodiment. FIG. 16A exemplifies a case where the respiratory cycle is relatively long (e.g., TR=about 4000 msec), and FIG. 16B exemplifies a case where the respiratory cycle is relatively short (e.g., TR=about 2000 msec).

As shown in FIG. 16A, when the TR is sufficiently long, the longitudinal magnetization components of a background tissue that are inverted because of the irradiation of the non-selective IR pulse sufficiently recover before the next TR starts. When the non-selective IR pulse is irradiated again in the next TR, because the longitudinal magnetization components of the background tissue are inverted from the sufficiently-recovered state, the time until the null point is the TI value of the background tissue.

On the other hand, as shown in FIG. 16B, when the TR is short, the longitudinal magnetization components of the background tissue that have been inverted because of the irradiation of the non-selective IR pulse cannot recover before the next TR starts. Accordingly, when the non-selective IR pulse is irradiated in the next TR, because the longitudinal magnetization components of the background tissue are inverted from the state of having recovered only to the middle, the time until the null point is shorter than the TI value of the background tissue. As shown in FIG. 16B, even if MR signals are acquired in the first TI, there is a possibility that the acquisition timing does not match the null point of the background tissue.

In this respect, even when the TR is short, by repeating the TR, the recovery process of the longitudinal magnetization components shown in FIG. 16B soon reaches the steady state so that it is possible to calculate an appropriate first TI for the short TR. For example, it suffices if, by performing experiments and simulations in advance, the corresponding relationship between the TR and an appropriate first TI is calculated and a table in which they are associated is stored in advance. Furthermore, it suffices if this table is prepared in accordance with the purpose of imaging, etc.

In this case, the sequence controlling circuitry 120 refers to the corresponding table in accordance with the information on, for example, the purpose of imaging (for example, Han angiogram of the hepatic artery) and acquires and sets a first TI corresponding to the respiratory cycle of the subject P in accordance with the information on the respiratory cycle of the subject P that is obtained during the breathing practice.

(Method of Calculation in Preparatory Scans)

A method of calculating a first TI and a second TI in preparatory scans will be described. As described above, it is preferable that, for the first TI, the time until the null point of the longitudinal magnetization components of the background tissue is set and, for the second TI, the time for the fluid present in the labeling region at the selective IR pulse irradiation timing to reach a desired position in the region of interest. Thus, preparatory scans may be performed while changing the first TI and the second TI and the resultant image and signal values may be analyzed automatically or manually by the operator to calculate appropriate first and second TI.

For example, the sequence controlling circuitry 120 performs preparatory scans at step S1 shown in FIG. 6. There are a preparatory scan of calculating the first TI and a preparatory scan of calculating the second TI. In the former case, for example, the sequence controlling circuitry 120 sets the second TI at a fixed value and, while changing the first TI per TR, acquires 2D images at one image/1TR. Thereafter, for example, the sequence controlling circuitry 120 analyzes the acquired multiple images, identifies an image with the highest contrast with the background tissue, and sets the first TI corresponding to the identified image for the first TI of imaging scan. Alternatively, for example, the sequence controlling circuitry 120 may display the acquired multiple images on the display 135 and may, by receiving identifying of an image from the operator, identify the image with the highest contrast with the background tissue.

Similarly, in the latter case, for example, the sequence controlling circuitry 120 sets the first TI at a fixed value and, while changing the second TI per TR, acquires 2D images at one image/1TR. Thereafter, for example, the sequence controlling circuitry 120 analyzes the acquired multiple images, identifies an image representing the highest degree at which the blood reaches, and sets the second TI corresponding to the identified image for the second TI for imaging scan. Alternatively, for example, the sequence controlling circuitry 120 may display the acquired multiple images on the display 135 and may, by receiving identifying of an image from the operator, identify the image representing the highest degree at which the blood reaches.

The preparatory scan method is not limited to the above-described method. For example, the sequence controlling circuitry 120 may sequentially acquire MR signals (for example, corresponding to one segment) in different lengths of time for the first TI (or different lengths of time for the second TI) in 1TR. In this case, the sequence controlling circuitry 120 may analyze the MR signals corresponding to the one segment to calculate the first TI, or display the analysis result on the display 135 and receive a specification from the operator. When MR signals corresponding to one image are acquired over multiple TRs, the sequence controlling circuitry 120 may generate an image per first TI in the same manner as the above-describe method, analyze the images, and display the images on the display 135 to identify a desired image.

Other Embodiments

Embodiments are not limited to the above-describe embodiments.

In the above-described embodiments, it is assumed that the region of interest is the hepatic artery, the portal vein, or the uterus; however, embodiments are not limited to them. For example, it is possible to similarly apply the above-described embodiments to imaging in which, for example, another site, such as the hepatic vein or the kidney, serves as the region of interest. In the above-described embodiments, it is assumed that the fluid is the blood; however, embodiments are not limited to this. For example, it is possible to apply the above-described embodiments to the cerebrospinal fluid (CSF), the lymph fluid, etc.

Furthermore, for example, for the above-described embodiments, the example has been described where the labeling region is set at one location; however, embodiments are not limited to this. The embodiments may be similarly applied to a case where the labeling region is set at multiple locations.

For the above-described embodiments, the example has been described where, after an RF pulse having a flip angle of 90 degrees is irradiated, an RF pulse having a flop angle of 180 degrees is irradiated; however, embodiments are not limited to this. For example, when MR signals are acquired by the FASE method, any one of the constant flop angle (CFA) method or the variable flop angle method (VFA) may be applied. In the CFA method, an RF pulse having arbitrary constant flop angles, such as a flip angle of 90 degrees and a flop angle of 120 degrees, are irradiated. On the other hand, in the VFA method, an RF pulse having a flop angle that varies according to the sweep pattern is irradiated. Furthermore, for example, when MR signals are acquired by using the balanced SSFP method, RF pulses having arbitrary flip angles, such as a degrees/2, α degrees, α degrees, . . . , and α degrees, that establishes the steady state are irradiated.

For the above-described embodiments, the example has been described where the imaging condition setting circuitry 133a, for example, displays the GUI and receives the inputs of the first TI and the second TI from the operator. As described above, the MRI apparatus 100 includes the GUI (also referred to as an operation circuitry) configurable of independent settings of the first TI and the second TI, and the MRI apparatus 100 receives input from the operator via the GUI. The GUI will be described with some examples. The GUI to be described below is applicable to any of the above-described embodiments.

Figure 17:
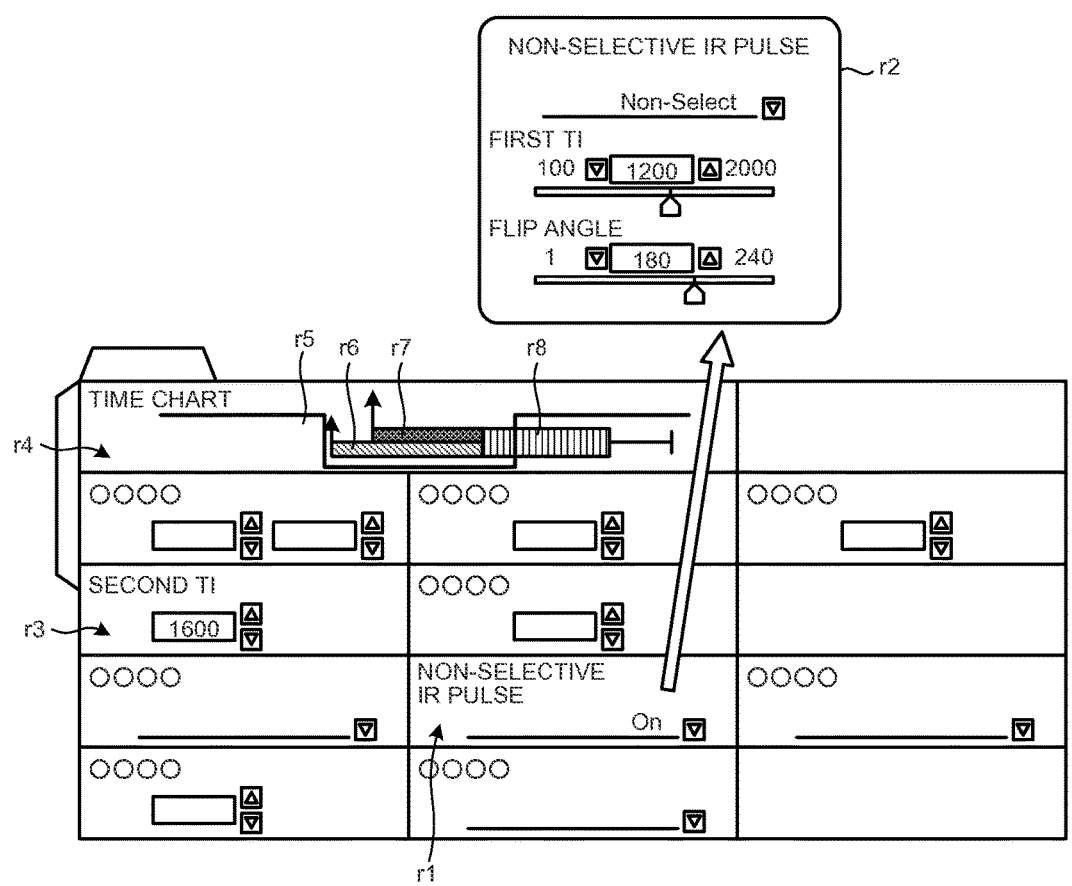
FIG. 17 is a diagram of explaining a GUI according to another embodiment.

FIG. 17 is a diagram of explaining a GUI according to another embodiment. The GUI shown in FIG. 17 is displayed at the timing at which settings of a labeling region and an imaging region on a localizer image are received from the operator (for example, the timing at step S2 shown in FIG. 6). The GUI shown in FIG. 17 shows, in a simplified manner, a part of the GUI that is displayed on the display 135. Although it is not shown in FIG. 17, for example, a localizer image or other setting screens may be displayed on the GUI.

For example, as shown in FIG. 17, on the GUI, operation tools for receiving settings of parameters for a pulse sequence to be executed are displayed. Some of the operation tools are displayed in a simplified manner. The types and arrangement of the operation tools are an example only. The GUI shown in FIG. 17 is an example where, for the first TI, first of all, an input of whether to irradiate the non-selective IR pulse (On or Off) in a region r1, another window r2 is then displayed according to the input of On, and an input of the first TI is received on the another window r2. For example, with the operation tools on the GUI shown in FIG. 17, it is possible to set a value from the minimum value of 100 msec to a maximum value of 2000 msec, for the first TI.

FIG. 17 shows the example where 11200 msec is input. Because it is possible to control the flip angle depending on the type of the non-selective IR pulse, as shown in FIG. 17, an operation tool of receiving a setting of a flip angle of a non-selective IR pulse may be displayed. The GUI shown in FIG. 17 is an example where an input is received in the region r3 for the second TI. Similarly to the case of the window r2, it is possible to display another window to receive the second TI.

Furthermore, for example, as show in FIG. 17, the GUI may be displayed together with a time chart r4. For example, when a pulse sequence is executed under the breath synchronization, for example, a waveform r5 representing the respiratory cycle is displayed on the time chart r4. On the time chart r4, for example, a rectangular sign r6 (the left end of the rectangular sign r6 corresponds to the selective IR pulse irradiation timing) representing the TI of the selective IR pulse (second TI), a rectangular sign r7 (the left end of the rectangular sign r7 corresponds to the non-selective IR pulse irradiation timing) representing the TI of the non-selective IR pulse (first TI), and a rectangular sign r8 (the left end of the rectangular sign r8 is the acquisition start timing) representing the acquisition of MR signals are represented. While independently setting the first TI and the second TI, the operator can check the relationship between the respiratory cycle and the MR signal acquisition timing on the time chart r4. On the time chart r4, the values of the first TI and the second TI that are currently set may be displayed.

The GUI shown in FIG. 17 is the example where, for both of the values of the first TI and the second TI, inputs from the operator are received; however, embodiments are not limited to this. The GUI may be one receiving the input of the second TI while the first TI is fixed at a fixed value. It is possible to independently set an arbitrary value for the second TI not in association with the fixed first TI. In this case, the GUI may, or does not necessarily display, the first TI. On the contrary, the GUI may be one receiving the input of the first TI while the second TI is fixed at a fixed value.

As described above, the MRI apparatus 100 includes the GUI configurable of independent settings of the first TI and the second TI. Another embodiment of the GUI will be described below.

In the above-described example shown in FIG. 17, the operation tools of receiving settings of parameters of a pulse sequence are displayed as the GUI and, as one type of settings of parameters, the example has been described where the inputs of the first TI and the second TI are received; however, embodiments are not limited to this.

There are MRI apparatuses 100 each capable of providing pulse sequence preset information to the operator. The pulse sequence preset information means default values being set in advance for each of the parameters for the pulse sequence. The pulse sequence preset information may be provided according to the purpose of imaging or provided simply as a variation. By selecting, for example, the preset information at the stage of imaging planning in a certain examination and customizing the selected preset information as required, the operator can complete settings of the pulse sequence suitable for the examination.

The imaging condition setting circuitry 133a displays preset information as the GUI configurable of independent settings of the first TI and the second TI and may receive a selection of preset information from the operator. For example, at the stage of imaging planning prior to step S1 shown in FIG. 6, the imaging condition setting circuitry 133a displays, as the GUI, a list of multiple sets of preset information that are prepared for imaging the hepatic artery. For example, the GUI displays preset information A and preset information B as a list. In the preset information A, for example, the first TI of 1200 msec and the second TI of 1600 msec are set in advance. On the other hand, in the preset information B, for example, the first TI 1200 msec and the second TI 1650 msec are set in advance. The operator selects desired preset information from among the prepared multiple sets of preset information.

For the above-described embodiments, the method of setting different lengths of time for the first TI according to the TR per individual has been described with reference to FIGS. 16A and 16B. For example, the imaging condition setting circuitry 133a may calculate the first TI corresponding to the TR of the subject P that is previously determined, the preset information in which the first TI may be regarded as a recommended preset information, and only the preset information may be displayed or the preset information may be displayed together with other set of preset information.

Furthermore, for example, a method can be considered in which, while the first TI is fixed at a fixed value, by repeatedly executing the pulse sequence for a few times while changing the second TI, an image is acquired from the MR signals acquired in each pulse sequence. In the multiple images in which the position that the fluid reaches gradually varies, the dynamics of the fluid appear. For example, for such a purpose of imaging, the imaging condition setting circuitry 133a displays the multiple sets of preset information that differ in the second TI in a list as the GUI. Accordingly, the operator can select all (or a part) of the multiple sets of preset information displayed in the list, as required.

(Specific Numerical Values and Order of Processing)

The specific numerical values exemplified according to the above-described embodiments (e.g., the numerical values of the first TI and the second TI, the TR of the breath synchronization, and the RR interval of the electrocardiogram synchronization) and the order of processing (e.g., the processing procedure shown in FIG. 6) are, in principle, an example only. The pulse sequence can be also changed arbitrarily.

(Program)

It is possible to execute the instructions represented in the processing procedures represented in the above-described embodiments based on a program that is software. The instructions described according to the embodiments are recorded as a computer-executable program in a magnetic disk, an optical disc, a semiconductor memory, or a recording medium equivalent to them. By reading the program from the recording medium and causing the CPU to execute the instructions described in the program according to the program, the computer realizes the same operations as those of the MRI apparatus 100 according to the embodiments. When acquiring or reading the program, the computer may acquire or read the program via a network.

With the magnetic resonance imaging apparatus according to at least one of the above-described embodiments, it is possible to improve the imaging power in non-contrast imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:

data storage configured to store, as preset MRI sequence controlling information, a first time and a second time, the first time defining elapsed time since a non-selective first RF (radio frequency) pulse until start of MR signal acquisition, the second time defining elapsed time since a selective second RF pulse applied to a labeling region until the start of MR signal acquisition, the second time also being a time required for a liquid present in the labeling region at a timing of the second RF pulse to reach peripheral blood vessels in an imaging region, the first time also being a time for longitudinal magnetization components of a background tissue to become substantially zero, the background tissue being in the imaging region and being other than a target of interest labeled by the selective second RF pulse, the first time and the second time being configured to be different according to a purpose of imaging to be performed by the preset MRI sequence controlling information;

image condition setting circuitry configured to display preset-able MRI sequence controlling information to a user;

sequence controlling circuitry configured to (a) set timings of the first RF pulse and the second RF pulse, based on preset information chosen by the user among information displayed by the image condition setting circuitry and (b) acquire magnetic resonance signals in the imaging region after a given time has passed since an RF pulse was applied to the labeling region; and image generating circuitry configured to generate an image using the magnetic resonance signals.

2. The magnetic resonance imaging apparatus according to claim 1, wherein the sequence controlling circuitry is configured to irradiate inversion recovery (IR) pulses inverting longitudinal magnetization components of a tissue as the first RF pulse and the second RF pulse.

3. The magnetic resonance imaging apparatus according to claim 1, wherein the labeling region is set in a position non-overlapping with a region of interest in the imaging region.

4. The magnetic resonance imaging apparatus according to claim 1, wherein the second time is longer than a time estimated based on a recovery time of the longitudinal magnetization components of the background tissue.

5. The magnetic resonance imaging apparatus according to claim 1, wherein the second time is a time inclusive of a desired number of systoles.

6. The magnetic resonance imaging apparatus according to claim 1, wherein the sequence controlling circuitry is configured to set different lengths of time for the first time according to TR (Repetition Time(s)).

7. The magnetic resonance imaging apparatus according to claim 1, wherein the target of interest is blood.

8. The magnetic resonance imaging apparatus according to claim 1, wherein a region of interest in the imaging region is liver tissue.

9. The magnetic resonance imaging apparatus according to claim 1, wherein a region of interest in the imaging region is tissue of an uterus.

* * * * *